(12) United States Patent
Jordan (10) Patent No.: US 8,986,316 B1
(45) Date of Patent: *Mar. 24, 2015

(54) POSITIONAL DUAL DRILL GUIDE

(71) Applicant: Christopher Jordan, Midwest City, OK (US)

(72) Inventor: Christopher Jordan, Midwest City, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 13/999,300

(22) Filed: Feb. 7, 2014

Related U.S. Application Data (63) Continuation-in-part of application No. 13/317,514, filed on Oct. 20, 2011.

(51) Int. Cl.
*A61B 17/17* (2006.01)

(52) U.S. Cl.
CPC .................................. *A61B 17/1714* (2013.01)
USPC ............................................................ 606/96

(58) Field of Classification Search
USPC .............. 606/86 R, 96–98; 33/333, 334, 512, 33/638, 642, 645; 403/61, 82
See application file for complete search history.

(56) References Cited

U.S. PATENT DOCUMENTS

| | | | |
|---|---|---|---|
| 4,672,957 A * | 6/1987 | Hourahane | 606/80 |
| 4,907,577 A | 3/1990 | Wu | |
| 5,163,940 A | 11/1992 | Bourque | |
| 5,562,664 A | 10/1996 | Durlacher | |
| 5,681,333 A | 10/1997 | Burkhart | |
| 5,688,284 A | 11/1997 | Chervitz | |
| 6,120,511 A | 9/2000 | Chan | |
| 6,342,056 B1 * | 1/2002 | Mac-Thiong et al. | 606/96 |
| 7,416,553 B2 | 8/2008 | Patel | |
| 7,520,880 B2 | 4/2009 | Claypool | |
| 7,758,582 B2 * | 7/2010 | Ferrante et al. | 606/96 |
| 7,833,230 B2 | 11/2010 | Cerundolo | |
| 7,955,341 B2 * | 6/2011 | Cerundolo | 606/148 |
| 8,439,925 B2 * | 5/2013 | Marino et al. | 606/87 |
| 2003/0216742 A1 | 11/2003 | Wetzler | |
| 2008/0103506 A1 * | 5/2008 | Volpi et al. | 606/96 |
| 2010/0121337 A1 | 5/2010 | Pandya | |
| 2011/0166581 A1 | 7/2011 | Van der Merwe | |

FOREIGN PATENT DOCUMENTS

FR 2 901 465 * 11/2007

* cited by examiner

*Primary Examiner* — Christian Sevilla
*Assistant Examiner* — Eric S Gibson
(74) *Attorney, Agent, or Firm* — Randal D. Homburg (57) ABSTRACT

A multi-positional dual drill guide for use in orthopedic surgical procedures provides two independent drill guides which are independently, pivotally and removably secured along a pivotal drill guide plate comprising two separate and independent guide plate sections, selectively aligning each of the two drill guides for drilling an intersecting bone channel into a common bone from different locations for the passage of a suture and associated tissue during an orthopedic repair of a joint. The drill guide provide for three dimensional movement of the drill guides to provide a range of drilling angles from nearly zero degrees up to 180-degrees apart and in a three dimensional array, the drill.

6 Claims, 7 Drawing Sheets

POSITIONAL DUAL DRILL GUIDE

CROSS REFERENCE TO RELATED APPLICATIONS

None

BACKGROUND OF THE INVENTION

1. Field of Invention

A multi-positional dual drill guide for use in orthopedic surgical procedures during an orthopedic repair of a joint, cartilage, bone or associated soft tissues, provides two independent drill guide to properly align a pair of holes being drilled into a common bone from different locations to intersect and form a common channel for the passage of a suture and associated tissue during an orthopedic repair of a joint wherein the suture or other repair material is passed through the bone tunnels with specially designed tools that work in conjunction with the drill guide.

2. Description of Prior Art

A preliminary review of prior art patents was conducted by the applicant which reveal prior art patents in a similar field or having similar use. However, the prior art inventions do not disclose the same or similar elements as the present full range multi-positional bone drill guide, nor do they present the material components in a manner contemplated or anticipated in the prior art.

In a first set of patents of prior art, singular drill guides are disclosed having a first fixed leg which defines a positioning guide, while a drill guide is adjustably affixed to an arched pathway to set the drill guide at a desired angle with the positioning guide. These patent include U.S. Pat. No. 6,342,056 to Mac-Thiong, U.S. Pat. No. 6,120,511 to Chan, U.S. Pat. No. 5,688,284 to Chervitz, U.S. Pat. No. 5,562,644 to Durlacher, U.S. Pat. No. 7,833,230 to Cerundolo, and U.S. Pat. No. 5,163,940 to Bourque. Three pending patent application have been published indicating a similar fixed indicator or pin with an adjustable drill guide, including U.S. Patent Application Publication Nos. 2011/0166581 to Van Der Merwe (Jul. 7, 2011), 2010/0121337 to Pandya (May 13, 2010), and 2003/0216742 to Wetzler (Nov. 20, 2003). In U.S. Pat. No. 4,672,957 to Hourahane, a single drill guide in shown providing a bracket of approximately 180 degree with a first support engaged upon the arced bracket providing a tubular drill guide, and a second support upon which a probe is located, the probe defining a pointed tip, which is visible to a surgeon during a repair to the knee joint, the pointed tip inserted to the desired depth into the knee joint.

There is a published patent application, U.S. Patent Application No. 2008/0103506 to Volpi, which indicates a dual drill guide mechanism with a first fixed drill guide and a second adjustable drill guide on curved support extending between the first and second guide members with the first and second drill guides being offset such that the axis of the guide members do not intersect. It also has a support arm in another embodiment and mated to the first guide member to mark the termination of the first drill guide passage. The support does not disclose a means of providing an angle to the support member allow the first and second drill guide to not only slide along the support member up to 180 degrees, but also up to 90 degrees in a perpendicular plane.

SUMMARY OF THE INVENTION

In orthopedic surgical procedures involving ligament or soft tissue repair, it is common practice to drill a channel in a bone from two locations which result in a complete and intersection bone channel through a segment of the bone. As seen previously, there are numerous bone drill guides in the prior art which furnish a single drill guide associated with a location probe which requires the drilling of a first bone channel and subsequent placement of the probe at a location wherein the second bone channel is drilled with the intent that the first and second bone channels intersect or that a terminal end of the bored bone channel can be predicted. Some of these prior art drill guides have a stationary probe with a drill guide movable along a two dimensional plane and upon a fixed arced plate, with some having both a movable probe and a movable drill guide in combination. However, none of them have a dual drill guide, nor do any of them contemplate a three dimensional capability for placement of two independently movable drill guides targeting a common intersecting point with the drill guides being aimed at the same time and drilled one after the other without movement of either drill guide resulting in a common and complete bone channel.

The present dual drill guide provides a pivotal guide plate with two guide plate sections pivotally connected at a pivot joint by a set screw allowing for a pivotal setting of between zero and one hundred eighty degrees with the pivotal joint providing complete separation of the two guide plate sections and also providing a locked and fixed position of each guide plate section at a location selected by the surgeon. In addition, each guide plate section provides an arced plate with a central sliding channel with independently sliding drill guide base members having anchor screws to secure each sliding drill guide base members at a location along each respective guide plate, each drill guide base member having a drill guide retained within a directed drill guide channel by a drill guide retaining screw providing an adjustable depth for each drill guide, the sliding drill guide base members being slidable along their respective guide plates to provide drill guide angles between ten degrees and one hundred eighty degrees within a three dimensional realm.

DESCRIPTION OF THE DRAWINGS

The following drawings are submitted with this utility patent application.

FIG. 6 is an exploded view of the components defining the dual drill guide along with a pair of drill bits.

DESCRIPTION OF THE PREFERRED EMBODIMENT

Figure 1:
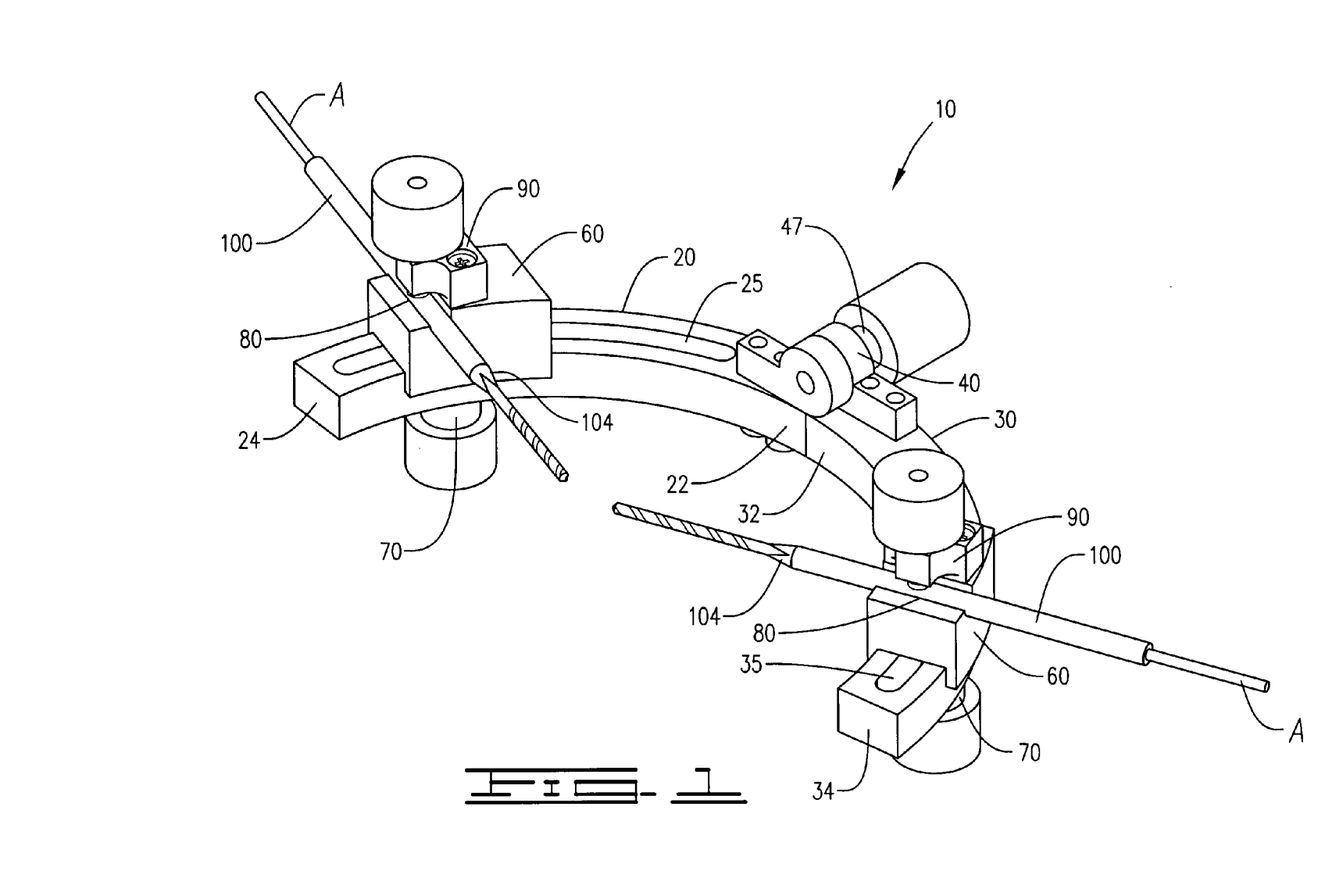
FIG. 1 is an upper perspective view of the dual drill guide showing drill bits inserted within the two drill guides.
Figure 5:
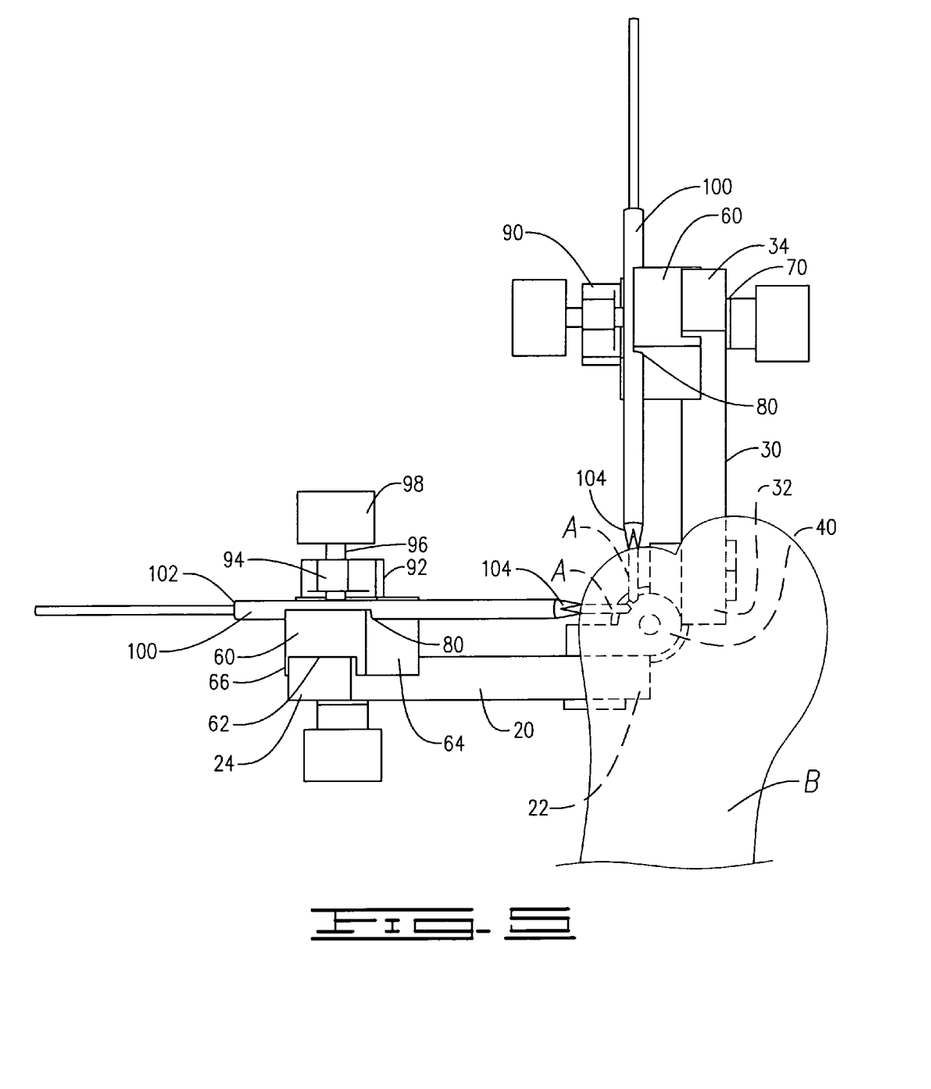
FIG. 5 is an end view of the dual drill guide with the tube anchor spikes of the drill guide tube directed upon the surface of the bone and having the drill bits as would be inserted into a bone, shown in phantom line with the joint bent at a ninety degree angle.

A three dimensional axis dual drill guide 10, as disclosed in FIGS. 1-7B of the drawings is used to align and bore two intersecting bone tunnels C within a bone B through two independent bone drill guides 100 contemporaneously set and positioned at locations upon a target bone to drill a transosseous channel D within the target bone for the further passage of a suture during a joint, cartilage, bone or associated soft tissue repair operation, the drill guide 10 further comprising a first guide plate 20 defining a flat circular arc, a joint end 22, a terminal end 24 and a central arced slide groove 25, a second guide plate 30 defining a flat circular arc, a joint end 32, a terminal end 34 and a central arced slide groove 35, each respective joint end pivotally connected by a joint 40 which can be disconnected, pivoted at an angle between 20 degrees and 180 degrees, and also secured to maintain an angle between the first guide plate 20 and the second guide plate 30 by a joint securing means 47, each first and second guide plate 20, 30 further providing a first and second slidable guide anchor 60 defining a lower slide trough 62 slidably engaging a respective first and second guide plate 20, 30 and being locked into an independent selected position along each respective guide plate 20, between said joint end 22, 32 and said terminal end 24, 34 within said central arced slide groove 25, 35 by an anchor locking means 70, each slidable guide anchor 60 further defining an upper tangential drill guide channel 80 and a drill guide locking means 90 which secures a respective drill guide tube 100 within each respective guide channel 80 by the drill guide locking means 90, FIGS. 1 and 5, each respective guide channel 80 directing a fixed relative angle between the respective drill guide tubes forming an angle of between 210 degrees and 20 degrees, the drill guide tube 100 through which bone drill bits A may be inserted to drill the intersecting bone channels B.

The joint 40 is further disclosed in FIG. 6 as having a first joint member 42 with a threaded extension 43 attached to the joint end 22 of the first guide plate 20, and a second joint member 44 forming an extension clip 45 which engages the threaded extension 44 of the first joint member 42, with the joint securing means 47 further defining a locking cap 48 which is threadably engaged upon the threaded extension 43, the locking cap 47 rotated to allow the joint 40 to be locked in place, allowing the joint 70 to move about an angle between 20 and 180 degrees, or further rotated to allow the first guide plate 20 and second guide plate 30 to be separated by the removal of the extension clip 45 from the threaded extension 43. Each first and second joint member 42, 44 may be respectively secured to the first or second guide plates 20, 30 using joint attaching screws 49 which attach independently through each respective first and second joint member 42, 44 into the respective first and second joint ends 22, 32 of each respective first and second guide plate 20, 30, FIG. 6.

Figure 2:
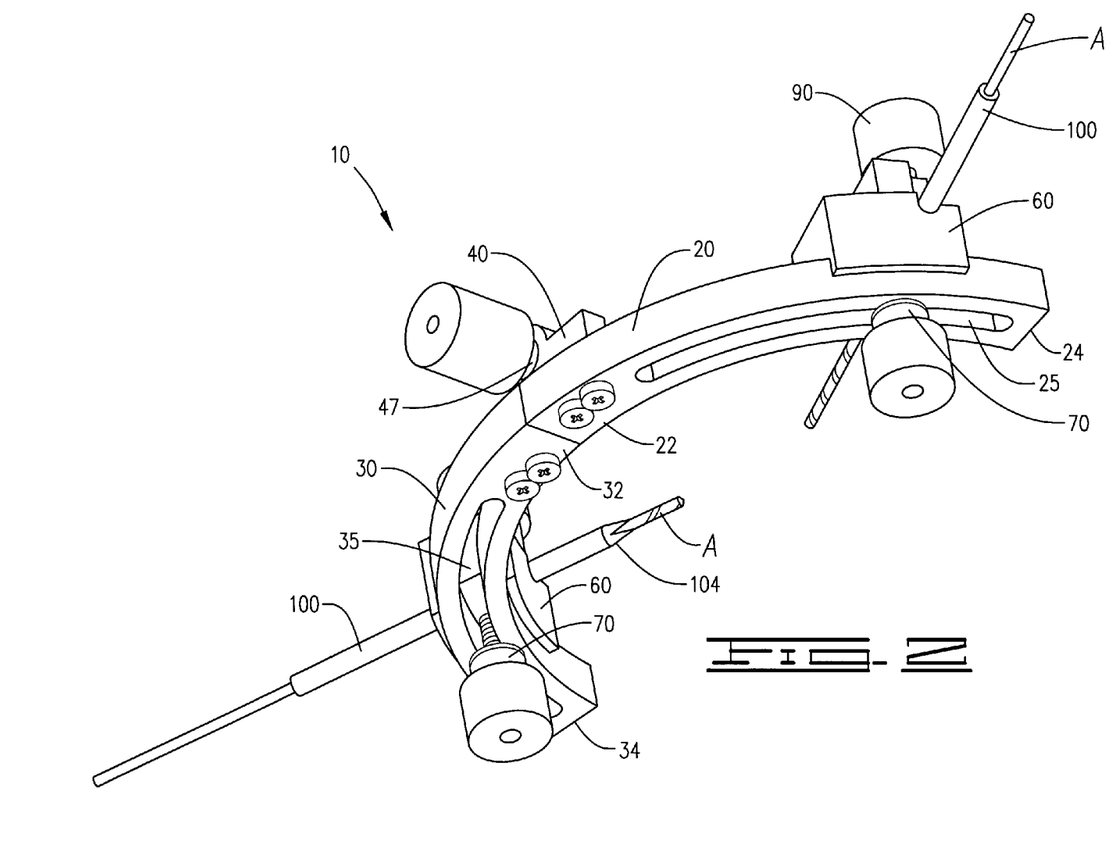
FIG. 2 is a lower perspective view of the dual drill guide.
Figure 3:
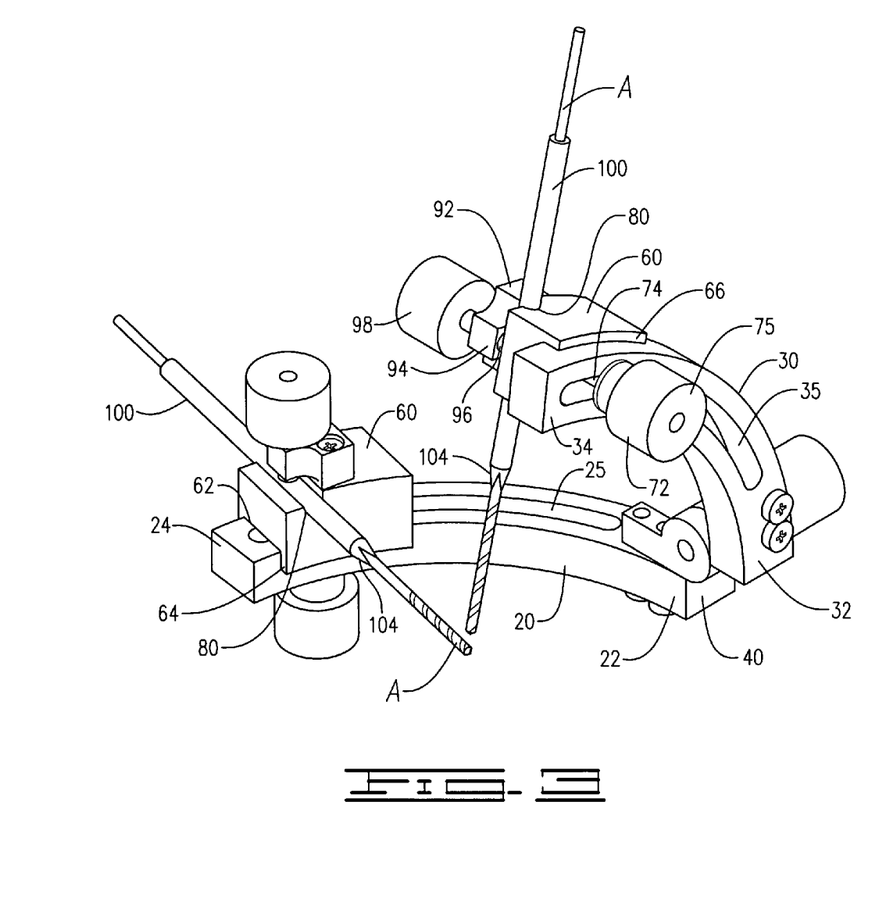
FIG. 3 is an upper perspective view of the dual drill guide with the joint bent at a right angle.
Figure 4:
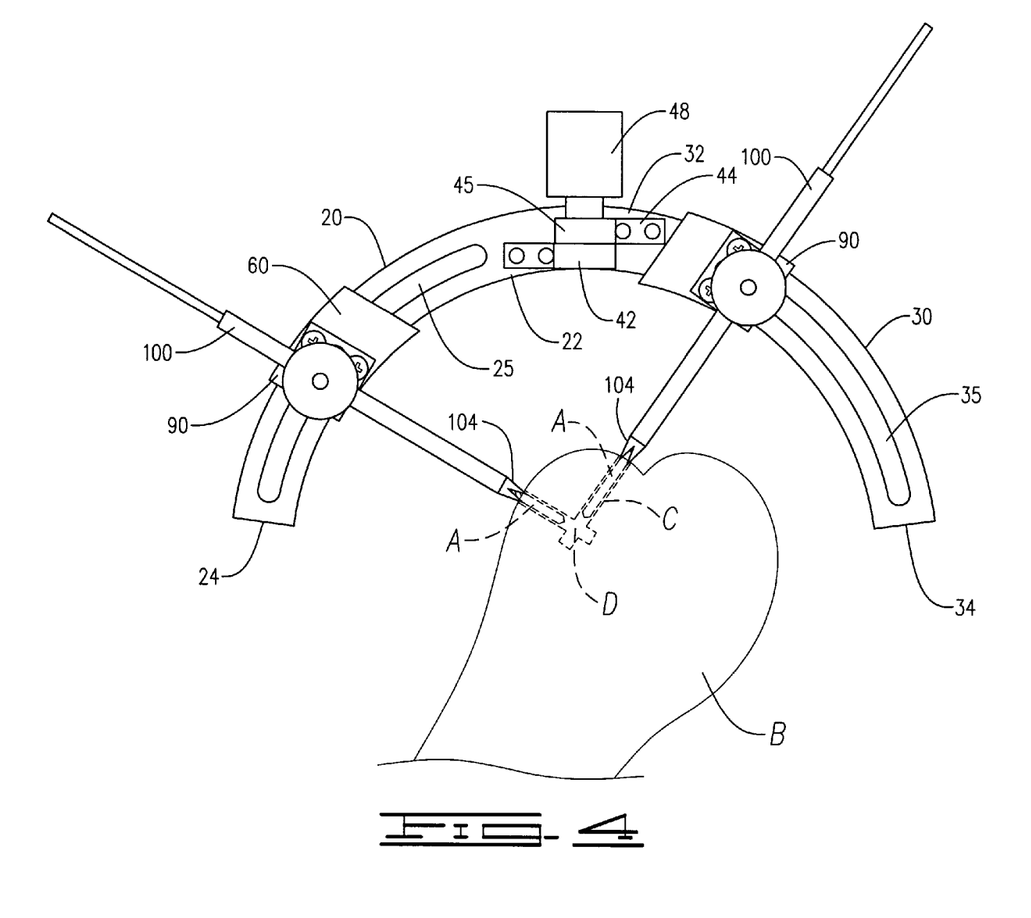
FIG. 4 is an upper view of the dual drill guide in a flat embodiment with the tube anchor spikes of the drill guide tube imbedded within the bone and having the drill bits inserted into a target bone with the penetrating portions of the drill bit, the bone tunnels and the transosseous channel shown in phantom line.

Each slidable guide anchor 60 may further define the lower slide trough 62 having an inner rail 64 and an outer rail 66, FIG. 2, each lower slide trough 62, inner rail 64 and outer rail 66 conforming to the arced contour of each first and second guide plate 20, 30, sliding freely upon each guide plate 20, 30, with each lower slide trough 62 further defining a lower threaded bore 68 into which the anchor locking means 70 may be secured to lock each guide anchor 60 at a desired location upon the guide plate 20, 30. The anchor locking means 70 may be further disclosed as a lower locking screw 72 having a threaded extension 74 engaging the lower threaded bore 68 of the guide anchor 60 through the respective central arced slide groove 25, 35 of each guide plate 20, 30, FIG. 2, the lower locking screw 72 having a head 75 which is rotated to lock or release the guide anchor 60 from a selected position to be moved to another.

Each guide anchor 60 also may further define the drill guide locking means 90, FIG. 1, having an upper channel block 92 with an extension arm 94 positioned above the drill guide channel 80, FIG. 5, the extension arm 94 providing a central lock screw bore 96 within which is inserted a lock screw 98 which is rotated to retain or release the drill guide tube 100 inserted within the drill guide channel 80 in a position desired prior to drilling a bone tunnel B through each drill guide tube 100 with a drill bit A. Each upper channel block 92 may be secured to the guide anchor 60 by removable block anchor screws 99, FIG. 6.

Figure 7A:
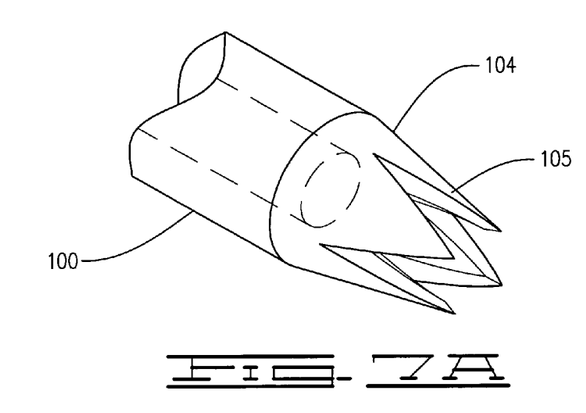
FIG. 7A is a close-up view of the tapered end of a drill guide tube defining the at least two tube anchor spikes.
Figure 7B:
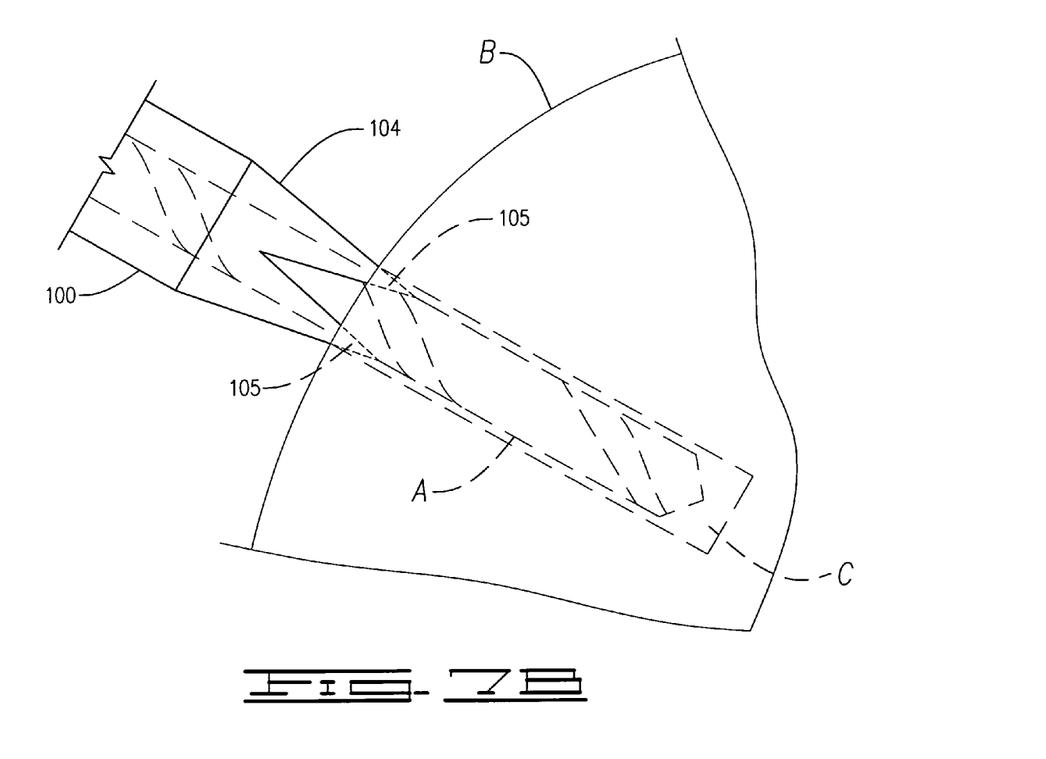
FIG. 7B is a close-up view of the at least two tube anchor spikes of the tapered end of the drill guide tube imbedded within the bone with the drill bit and the bone tunnel shown in phantom line.
Figure 8:
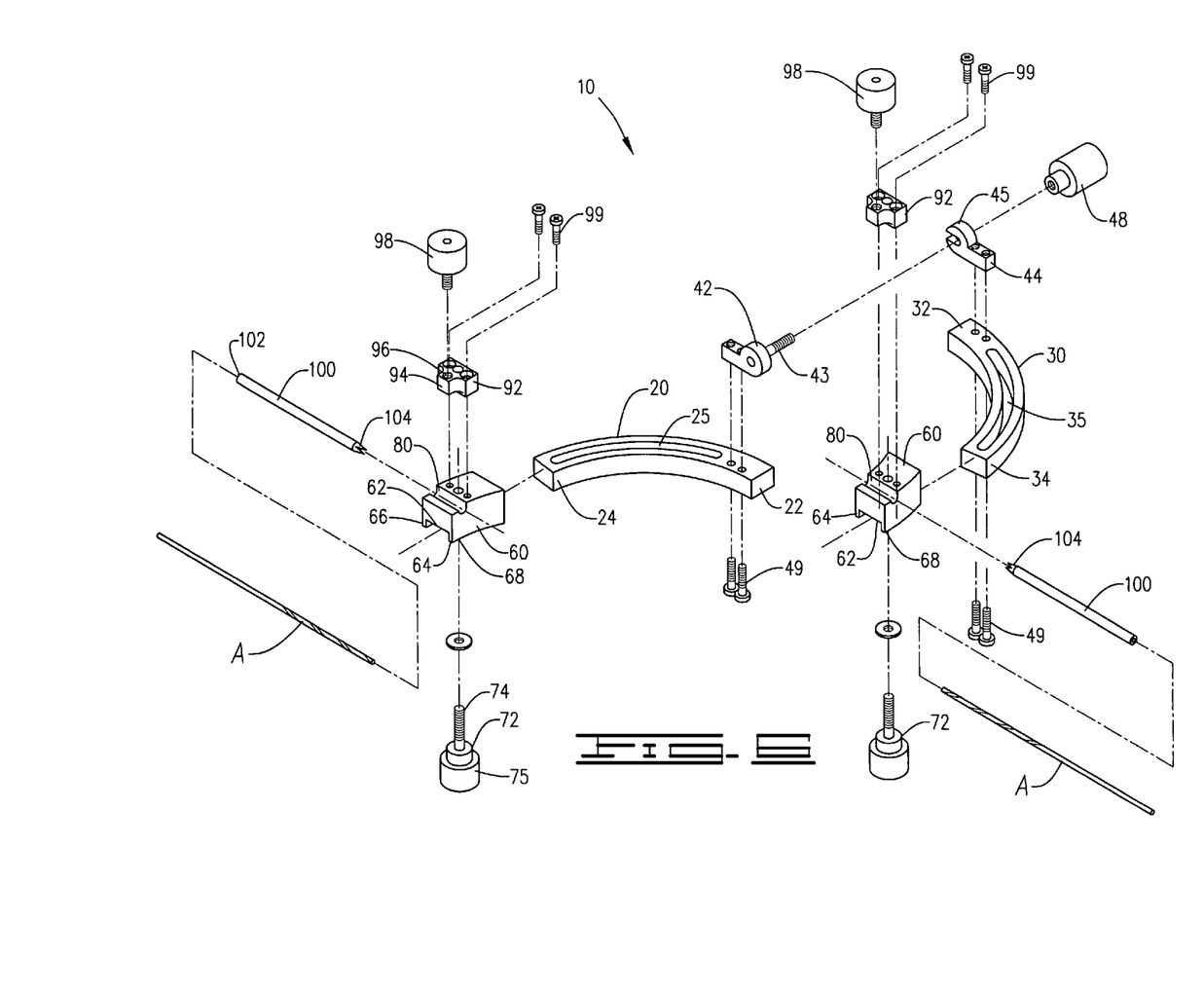

The drill guide tube 100 as contemplated for use within the dual drill guide 10 and as disclosed in FIGS. 1-7B of the drawings, is the type of drill guide tube 100 which defines a central bore 102 and has a tapered end 104 which is directed towards the target bone B, with a standard surgical bone drill bit A, also disclosed in FIGS. 1-7B of the drawings, being directed through the central bore 102 of the drill guide tube 100 out the tapered end 104. The drill guide tube 100 should be of a sufficient strength the withstand the pressure of being secured between the drill guide channel 80 and the drill guide locking means 90 without deforming the drill guide tube 100 during use and most preferably, repeated use. The drill guide tube 100 further defines at least two tube anchor spikes 105, FIG. 7A, defined within the tapered end 104 of the drill guide tube 100. As shown in FIG. 7B, these at least two tube anchor spikes 105 are tapped into the bone B at the location upon the bone B where the respective bone tunnels C are to be drilled to anchor the drill guide tube 100 within the bone B once the bone tunnel C placement has been determined by the surgeon prior to the application of the drill guide locking means 90. These at least two tube anchor spikes 105 prevent any skipping of the drill bit A when the drilling of the bone B is commenced and secures the target location on the bone B, stabilizing the drill guide 10 during use. The drawing figures show four tube anchor spikes 105 on the tapered end 104 of the drill tube 100, but the actual number of tube anchor spikes 105 can be as few as two.

It is further contemplated that the dual drill guide 10 could be supplied with a fixed positioning device which could retain the dual drill guide 10 at an external location once the dual drill guide is set to the drill angles upon the target bone location. With this additional fixed positioning device, the dual drill guide 10 may be equipped with a connecting apparatus to join with the fixed positioning device. It is also noted that the embodiment shown in the drawing figures is a best mode presentation based upon the known success of the dual drill guide 10 in prototype and anticipated use, with the dual drill guide materials suited for repeated use, post surgical clean-up and sanitization, and also for the replacement of parts when they become worn or broken. In this regard, the presentation of the dual drill guide 10 would be of stainless steel or other biocompatible metal suitable for use in an open surgical procedure.

It is the intent of the dual drill guide 10 to be used as indicated above for the contemporaneous positioning of two intersecting bone tunnels C without having to reposition the drill guide, as seen in the various prior art single drill guides, and to maintain the position of the two drill guide tubes 100 for assured intersection regardless of the positioning of the drill guide tubes 100 upon the guide plates 20, 30 of the dual drill guide 10, FIGS. 1-5. In furtherance of this intent, the use of the dual drill guide 10 would require preparation of the surgical site to expose the target bone location for the occurrence of the transosseous channel for a surgical repair. Once the site is prepared, the dual drill guide 10 is positioned over the prepared site and the first drill guide tubes 100 (or either of drill guide tube, because a designation of a first and second drill guide tube is irrelevant at this point) is positioned along the corresponding guide plate where the drill guide tube is aligned with the intended first bone tunnel C. The first and second guide plates 20, 30 are then secured at the appropriate selected angle to position the second drill guide tube 100 at a position and location with the intended second bone tunnel C, with the dual drill guide 10 maintaining the drill guide tubes 100 in intersecting relationships regardless of the relevant positions along the first and second guide plates 20, 30. Once established and set, the drill guide tubes 100 provide the fixed selected position of the two drill guide tubes 100 for the drilling of the two bone channels C by the drill bits A to form the appropriate transosseous channel D within the target bone B to ensure a complete intersecting pathway of the two drilled bone tunnels C to complete the portion of the surgery and the passage of a suture through the transosseous channel C within the target bone B. Upon completion, the surgeon may remove the dual drill guide 10 or reposition the dual drill guide 10 for a second drilling location. This dual drill guide 10 is forseen as providing a useful tool in shoulder, knee and other joint repair surgeries.

Therefore, a method for using the dual drill guide 10 as disclosed would include the steps of preparing a location for a joint repair by exposing a target bone, positioning the drill guide above the target bone, setting each first and second drill guide tubes at a desired angle and position upon the target bone, drilling each bone tunnel using a drill bit to form the intersecting transosseous channel, using specially prepared suture passing instruments to insert and pass the repair sutures through the prepared holes and completing the joint repair using the steps known in the art of orthopedic surgery for the joint repair, the dual drill guide providing the angle drill tubes to drill two independent bone tunnels forming the transosseous channel within the bone a desired depth without requiring the repositioning of the dual drill guide upon the bone.

While the invention has been particularly shown and described with reference to a preferred embodiment thereof, it will be understood by those skilled in the art that changes in form and detail may be made therein without departing from the spirit and scope of the invention.

What is claimed is:

1. A three dimensional axis dual drill guide used to align and bore two intersecting bone tunnels within a target bone through two independent bone drill guides contemporaneously set and positioned at locations upon said target bone to drill a transosseous channel within said target bone for further passage of a suture during a joint, cartilage, bone or associated soft tissue repair operation, said drill guide further comprising:
    a first guide plate defining a flat circular arc, a joint end, a terminal end and a central arced slide groove;
    a second guide plate defining a flat circular arc, a joint end, a terminal end and a central arced slide groove, each respective joint end pivotally of each said first and second guide plates connected by a joint which can be disconnected, pivoted at an angle between 180 degrees and 20 degrees, and also secured to maintain an angle between said first guide plate and said second guide plate by a joint securing screw;
    a first and second slidable guide anchor defining a lower slide trough slidably engaging each respective first and second guide plate and being locked into an independent selected position along each respective guide plate by an anchor locking screw, each slidable guide anchor further defining an upper tangential drill guide channel and a drill guide locking screw which secures a respective drill guide tube within each said respective guide each said drill guide tube forming a tapered end defining at least two tube anchor spikes which are directed into the target bone at respective locations chosen by the surgeon, each said guide channel directing a fixed relative angle between said respective drill guide tubes capable of forming an angle of between 210 degrees and 20 degrees between said drill guide tubes through which bone drill bits are inserted to drill said intersecting bone channels within said target bone.

2. The dual drill guide, as disclosed in claim 1, further comprising:
    said joint defining a first joint member with a threaded extension attached to said joint end of said first guide plate, and a second joint member forming an extension clip which engages said threaded extension of said first joint member; and
    said joint securing screw further defining a locking cap which is threadably engaged upon said threaded extension, said locking cap rotated to allow said joint to be locked in place, allowing said joint to move about an angle between 20 and 180 degrees, or further rotated to allow said first guide plate and second guide plate to be separated by removal of said extension clip from said threaded extension.

3. The dual drill guide as disclosed in claim 1, wherein each slidable guide anchor further comprising:
    each of said lower slide trough defining an inner rail and an outer rail, each said lower slide trough, inner rail and outer rail conforming to the width and arc each respective said first and second guide plates, sliding freely upon each said guide plate, with each of said lower slide trough further defining a lower threaded bore into which said anchor locking screw is secured to lock each said guide anchor at a selected position upon each said guide plate; and
    each of said anchor locking screw defining a lower locking screw having a threaded extension engaging said respective lower threaded bore of said respective guide anchor through said respective central arced slide groove of each said respective guide plate, said lower locking screw having a head which is rotated to lock or release said guide anchor from said selected position to another selected position.

4. The dual drill guide as disclosed in claim 1, wherein each said guide anchor further comprising said drill guide locking screw defining an upper channel block with an extension arm positioned above said drill guide channel, said extension arm including a central lock screw bore within which is inserted a lock screw which is rotated to retain or release said drill guide tube inserted within said drill guide channel in a selected extension position prior to drilling said bone tunnel through each said drill guide tube.

5. The dual drill guide as disclosed in claim 1, wherein each slidable guide anchor further comprising:
    each of said lower slide trough defining an inner rail and an outer rail, each said lower slide trough, inner rail and outer rail conforming to the width and arc of each respective said first and second guide plates, sliding freely upon each said guide plate, with each said lower slide trough further defining a lower threaded bore into which said anchor locking screw is secured to lock each said guide anchor at a selected position upon each said guide plate, and each of said anchor locking screw defining a lower locking screw having a threaded extension engaging said respective lower threaded bore of said respective guide anchor through said respective central arced slide groove of each said respective guide plate, said lower locking screw having a head which is rotated to lock or release said guide anchor from said selected position to another selected position; and said drill guide locking screw defining an upper channel block with an extension arm positioned above said drill guide channel, said extension arm including a central lock screw bore within which is inserted a lock screw which is rotated to retain or release said drill guide tube inserted within said drill guide channel in a selected extension position prior to drilling said bone tunnel through each said drill guide tube.

6. The dual drill guide as disclosed in claim 1, further comprising:

said joint defining a first joint member with a threaded extension attached to said joint end of said first guide plate, and a second joint member forming an extension clip which engages said threaded extension of said first joint member, and said joint securing screw further defining a locking cap which is threadably engaged upon said threaded extension, said locking cap rotated to allow said joint to be locked in place, allowing said joint to move about an angle between 20 and 180 degrees, or further rotated to allow said first guide plate and second guide plate to be separated by removal of said extension clip from said threaded extension;

each of said lower slide trough defining an inner rail and an outer rail, each said lower slide trough, inner rail and outer rail conforming to the width and arc each respective said first and second guide plates, sliding freely upon each said guide plate, with each said lower slide trough further defining a lower threaded bore into which said anchor locking means is secured to lock each said guide anchor at a selected position upon each said guide plate, and each of said anchor locking screw defining a lower locking screw having a threaded extension engaging said respective lower threaded bore of said respective guide anchor through said respective central arced slide groove of each said respective guide plate, said lower locking screw having a head which is rotated to lock or release said guide anchor from said selected position to another selected position; and each of said drill guide locking screw defining an upper channel block with an extension arm positioned above said drill guide channel, said extension arm including a central lock screw bore within which is inserted a lock screw which is rotated to retain or release said drill guide tube inserted within said drill guide channel in a selected extension position prior to drilling said bone tunnel through each said drill guide tube.

\* \* \* \* \*